United States Patent [19]
Savage et al.

[11] Patent Number: 5,830,209
[45] Date of Patent: Nov. 3, 1998

[54] MULTI-FIBER LASER CATHETER

[75] Inventors: Steven D. Savage, Brooklyn Center; Gregory G. Brucker, Minneapolis, both of Minn.

[73] Assignee: Angeion Corporation, Plymouth, Minn.

[21] Appl. No.: 529,810

[22] Filed: Sep. 18, 1995

Related U.S. Application Data

[63] Continuation-in-part of Ser. No. 129,545, Sep. 28, 1993, abandoned, which is a continuation of Ser. No. 831,524, Feb. 5, 1992, abandoned.

[51] Int. Cl.[6] .................................................. A61B 17/36
[52] U.S. Cl. ........................ 606/15; 606/16; 606/13; 607/122
[58] Field of Search .................... 606/2, 3, 7, 13–16; 607/100–102, 88, 89, 115, 116, 122

[56] References Cited

U.S. PATENT DOCUMENTS

| | | |
|---|---|---|
| 3,858,577 | 1/1975 | Bass et al. . |
| 4,266,549 | 5/1981 | Kimura . |
| 4,360,031 | 11/1982 | White . |
| 4,506,680 | 3/1985 | Stokes . |
| 4,577,642 | 3/1986 | Stokes . |
| 4,592,353 | 6/1986 | Daikuzono . |
| 4,660,571 | 4/1987 | Hess et al. ............................... 607/116 |
| 4,669,467 | 6/1987 | Willett et al. . |
| 4,718,417 | 1/1988 | Kittrell et al. . |
| 4,784,133 | 11/1988 | Mackin . |
| 4,785,806 | 11/1988 | Deckelbaum . |
| 4,785,815 | 11/1988 | Cohen ......................................... 606/7 |
| 4,791,926 | 12/1988 | Fry . |
| 4,832,024 | 5/1989 | Boussignac et al. . |
| 4,834,093 | 5/1989 | Littleford . |
| 4,844,062 | 7/1989 | Wells . |
| 4,844,099 | 7/1989 | Skalsky et al. . |
| 4,850,351 | 7/1989 | Herman et al. . |
| 4,862,887 | 9/1989 | Weber . |
| 4,890,898 | 1/1990 | Bentley . |
| 4,917,106 | 4/1990 | Olivier . |
| 4,940,064 | 7/1990 | Desai ...................................... 607/122 |
| 4,985,028 | 1/1991 | Isner et al. . |
| 4,997,431 | 3/1991 | Isner et al. ............................... 606/15 |
| 5,002,067 | 3/1991 | Berthelsen et al. . |
| 5,003,990 | 4/1991 | Osypka . |

(List continued on next page.)

FOREIGN PATENT DOCUMENTS 3617019 11/1987 Germany .

OTHER PUBLICATIONS

Willkampf, F. H. et al. "Radiofrequency Ablation with a Cooled Porous Electrode Catheter," Abstract, JACC vol. 11, No. 2, pp. 17A, 1988.

Huang, et al. "Increase in the Lesion Size and Decrease in the Impedance Rise with a Saline Infusion Electrode Catheter for Radiofrequency Catheter Ablation," Abstract, Circulation, vol. 80, No. 4, pp. II–324, 1989.

Ruffy, Rudolphe. "Radiofrequency Delivery Through an Endocardial Coded Catheter Results in Increased Lesion Size," Abstract, Circulation, vol. 88, No. 4, Part 2, 1993.

Bergau, Dennis. "Porous Metal Tipped Catheter Produces Larger Radiofrequency Lesions Through Tip Cooling," Abstract, Circulation, vol. 88, No. 4, p. 2, 1993.

Article entitled "Pacific Sintered Metals".

Dialog summary of abstracts and titles in the scientific and medical device databases, pp. 1–9.

*Primary Examiner*—Michael Peffley
*Attorney, Agent, or Firm*—Patterson & Keough, P.A.

[57] ABSTRACT

Laser catheters according to the invention include multiple optical fibers for delivery of laser energy to a pre-determined treatment site in the therapeutic treatment of cardiac tissue. A fixation device fixes the distal end of the catheter to the treatment site. Temperature sensing devices disposed on the fixation device provide a temperature depth profile of the tissue treatment site, which can be used to control the treatment. Multi-piece, single-piece and porous tip catheters are disclosed.

43 Claims, 7 Drawing Sheets

U.S. PATENT DOCUMENTS

| | | | |
|---|---|---|---|
| 5,026,367 | 6/1991 | Leckrone et al. | |
| 5,041,109 | 8/1991 | Abela . | |
| 5,041,121 | 8/1991 | Wondrazek et al. | |
| 5,053,033 | 10/1991 | Clarke | 606/7 |
| 5,057,099 | 10/1991 | Rink . | |
| 5,066,292 | 11/1991 | Müller et al. | |
| 5,092,864 | 3/1992 | Hayes et al. | |
| 5,106,386 | 4/1992 | Isner et al. | |
| 5,169,396 | 12/1992 | Dowlatshahi . | |
| 5,179,962 | 1/1993 | Dutcher et al. | |
| 5,188,635 | 2/1993 | Radkte . | |
| 5,192,278 | 3/1993 | Hayes et al. | 606/15 |
| 5,193,526 | 3/1993 | Daikuzono | 606/15 |
| 5,217,028 | 6/1993 | Dutcher et al. | |
| 5,242,441 | 9/1993 | Avitall . | |
| 5,246,436 | 9/1993 | Rowe . | |
| 5,281,212 | 1/1994 | Savage et al. | 606/15 |
| 5,281,213 | 1/1994 | Milder et al. | 606/15 |
| 5,313,943 | 5/1994 | Houser et al. | |
| 5,318,014 | 6/1994 | Carter . | |
| 5,323,781 | 6/1994 | Ideker et al. | |
| 5,324,284 | 6/1994 | Imran | 607/122 |
| 5,334,193 | 8/1994 | Nardella . | |
| 5,358,479 | 10/1994 | Wilson . | |
| 5,363,861 | 11/1994 | Edwards et al. | |
| 5,364,352 | 11/1994 | Cimino et al. | |
| 5,368,592 | 11/1994 | Stern et al. | |
| 5,370,678 | 12/1994 | Edwards et al. | |
| 5,383,923 | 1/1995 | Webster, Jr. et al. | |
| 5,391,147 | 2/1995 | Imran et al. | |
| 5,395,315 | 3/1995 | Griep . | |
| 5,397,342 | 3/1995 | Heil, Jr. et al. | |
| 5,423,805 | 6/1995 | Brucker et al. | 606/15 |
| 5,423,811 | 6/1995 | Imran et al. | |
| 5,500,012 | 3/1996 | Brucker et al. | 606/7 |

MULTI-FIBER LASER CATHETER

CROSS REFERENCES TO RELATED APPLICATIONS

This is a continuation-in-part of U.S. patent application Ser. No. 08/129,545, filed Sep. 28, 1993, now abandoned, which is a continuation of U.S. patent application Ser. No. 07/831,524, filed Feb. 5, 1992, now abandoned.

BACKGROUND OF THE INVENTION

1. Field of the Invention

The present invention pertains to a medical device and, more particularly, pertains to a catheter with optical fibers for carrying energy in the form of electromagnetic radiation, preferably laser radiation, to a site within a patient where there is tissue to be treated with that radiation.

2. Description of Related Art

The health industry has long recognized the potential therapeutic applications of laser energy. A common medical application of lasers is in the irradiation of tissue, both internal and external. For external treatment, the laser energy may be directly applied. However, where a procedure requires irradiation of internal tissues that are not readily accessible to external energy sources, the use of catheter-type devices to deliver coherent radiation to the treatment site is common. Typical applications requiring use of laser catheters are found in the treatment of various anatomical structures and conditions within the cardiovascular system. One type of treatment application, falling under the general heading of electrophysiological treatments, is exemplified by U.S. Pat. Nos. 4,997,431 and 4,985,028, both issued to Isner et al., for treatments within the heart itself, as opposed to the vascular system. An alternative category of cardiovascular applications come under the general heading of cardiological, where laser catheters have been successfully utilized to treat deposits caused by plaque build-up within the vascular system. For example, U.S. Pat. Nos. 5,041,109 to Abela and 4,718,417 to Kittrell et al. disclose the use of laser catheters to remove deposits within arteries.

It is important to appreciate here that the two types of applications described above for the use of laser catheter systems impose considerably different design and operational constraints on the catheters used for the application. This is due, in large part, to limitations imposed by the nature of the tissue to be treated as well as physical constraints imposed by the anatomical structures within which treatment is designed to be delivered. For example, in cardiological applications of laser catheters where the laser energy is used to break up deposits within arterial systems, laser catheter design can be somewhat simplified. In a typical procedure involving the use of such catheters, the device is introduced surgically into the vascular system and is advanced through vascular structures until an obstruction blocks further progress. At that point, laser energy is directed toward the obstruction site in an attempt to essentially burn away the deposits, resulting in their total destruction. The mechanism of energy transfer to the deposits can be through direct irradiation, or it can be indirect, through contact with a metal tip structure in the catheter that has been heated by a portion of the laser energy. See U.S. Pat. Nos. 5,041,109 to Abela and 4,718,417 to Kittrell et al. Delivery of laser energy is generally continued until it is once again possible for the catheter device to progress further though the vascular structure. Thus, it is generally unnecessary for such catheters to utilize means for mapping the location of the catheter or the nature of the tissue to be treated. Nor is it necessary for such catheters to employ sensing means to determine the extent of tissue treatment, as that is easily determined physically by the ability or the inability of the device to progress further through the vascular structure.

An important element of any medical procedure using catheter devices to deliver laser radiation to internal tissue sites for electrophysiological applications is the requirement for maneuvering the catheter device through the vascular system to reach the precise treatment site within the heart. In order to more precisely control this maneuvering of the catheter, it is convenient to utilize a guide wire or a multi-purpose guide/fixation wire to position the catheter. The above-referenced patents issued to Isner et al., and specifically incorporated herein by reference, teach the use of wires for the purposes of guiding a catheter through the vascular system to the tissue treatment site and for maintaining the position of the catheter once at the site.

The irradiation of tissue must be accomplished with great precision as the danger of also irradiating other adjacent tissue is always present, especially when the process occurs remotely at the distal end of a relatively long catheter. U.S. Pat. No. 4,785,806 issued to Deckelbaum discusses a system whereby an attempt is made to distinguish different types of tissue using ultraviolet fluoroscopy. A similar approach is proposed in U.S. Pat. No. 4,718,417 issued to Kittrell et al. Spectral analysis of reflected light energy is also proposed in U.S. Pat. No. 4,669,467 issued to Willett et al., wherein analytically significant wavelengths of light are delivered to the tissue in proximity to the distal end of the catheter system, and either scattered light or fluorescence is monitored as an indicator of the presence of tissue to be treated.

As will be recognized by one of skill in the art, laser catheters, such as that of the invention disclosed herein, are adapted for use in a multi-part system. In such a system a first, or outer, catheter is inserted into the patient and guided to the approximate treatment site within the heart, often aided by mechanical steering means. Such outer catheters also typically include means such as electrodes for surveying the electrophysiological characteristics of cardiac tissue to create a general map of the area to be treated. Catheters such as those embodied in the invention disclosed herein are then inserted within the outer catheter, and the laser optics brought into close proximity to the general tissue treatment site.

However, none of the prior art approaches to the use of catheter systems to deliver radiation to a tissue treatment site use a monitoring signal other than for the location and/or mapping of potential target tissue. Furthermore, none of the prior art implementations of laser irradiation catheters are capable of dynamically monitoring the operation of the irradiation activity itself. The prior art solely discusses either distinguishing the tissue to be treated from normal tissue prior to treatment, or analyzing the products of the procedure following irradiation. During laser catheter treatments, it is the production and absorption of laser and radio frequency radiation that produce the controlled heating that actually treats the unwanted tissues. References such as U.S. Pat. No. 4,785,815 to Cohen disclose the use of temperature sensing means within the catheter tip that monitors the catheter tip temperature. However, such monitoring can only provide information on whether the temperature of the catheter tip has reached a sufficient level to effectively treat the target tissue. In the case of the Cohen device, that target tissue comprises deposits within the vascular system, and not cardiac tissue within the heart. It is physically impossible for such temperature sensing means to provide an indication of the temperature of the tissue being treated.

Most importantly, none of the available prior art references indicate a capability to dynamically measure the physiological and thermal effects of irradiation activity on the treated tissue directly during the treatment process. Significantly, the prior art also fails to teach or make any suggestion that such dynamic monitoring of the affected tissue during treatment can be used to control the administration of the treatment itself.

Monitoring of the tissue temperature during treatment can be important. For the majority of laser catheter treatments concerned with removing arterial blockages, and even for the ablation of cardiac tissue, temperature monitoring can be less critical. During ablation, the laser energy essentially totally vaporizes the target tissue to achieve the desired therapeutic goals of the procedure. However, the use of the term ablation in the context of electrophysiological laser applications, although common, is essentially a misnomer. Such complete destruction of target tissue, with the exception of certain narrow and specific cardiac treatments, is limited to cardiological applications. In those applications, only a minimum temperature sufficient to ablate the tissue need be reached. However, in electrophysiological applications of laser catheters, the different physiological goals of treatment impose far different demands on laser catheter design. In such applications, the goal of the treatment is not the total destruction of target tissue (ablation), but the controlled denaturation of tissue to affect its electrophysiological properties. Here, the monitoring of temperature becomes extremely important lest unwanted destruction of the tissue occur. Within the heart, variations in cardiac tissue characteristics, perhaps as the result of scarring from previous cardiac trauma, can present vastly different tissue that react differently to the laser energy source. The absorption characteristics of the normal tissue can be much different from heavily scarred tissue. As a result, temperatures of the tissue surface where the laser energy is incident can be much higher for some tissue than for others. However, no prior art references disclose means capable of temperature monitoring to produce a signal capable of indicating the progress of treatment or, more importantly, that treatment should cease, such as upon detection of pre-determined temperatures within the tissue undergoing treatment.

An additional distinction exists between those procedures designed to clear deposits within the vascular system and those designed to alter the conductive characteristics of cardiac tissue. When a laser catheter is used within the vascular system to remove an occlusion, the distal end of the catheter is typically passed through the vascular structure until it simply encounters the target occlusion, which impedes further progress of the catheter. Laser energy is then directed at the occlusion mass until passage through the vascular structure is obtained. In such circumstances, precise focusing of the laser energy is not critical because the entire tissue mass within the radiation field of the catheter constitutes the target tissue. In the denaturation of endocardial tissue through use of laser energy, the precise focusing of the light beam becomes more important, particularly with multi-fiber catheter systems that typically produce a beam of wider cross-section to irradiate a larger area of tissue at one time. In the treatment of cardiac tissue, the dynamic state of the heart tissue further complicates the situation in that the heart is constantly moving during treatment. Thus, the use of fixation means to maintain the position of the distal end of the laser catheter with respect to the target tissue site can be extremely advantageous. Such means is used in the above-referenced patents issued to Isner.

Considerable advantages can be realized through the use of fixation means in the treatment of endocardial tissue with laser catheters, particularly when coupled with temperature sensing means capable of dynamically monitoring the temperature of the tissue undergoing treatment. These and other advantages will be apparent from the Detailed Description given below.

SUMMARY OF THE INVENTION

The general purpose of the present invention is to provide a laser and/or radio frequency irradiation catheter with a multiple-fiber laser or irradiation assembly including a temperature sensing means, a cooling means and a flushing means wherein the temperature sensing means provides a signal that can be used to dynamically monitor and control the tissue irradiation process.

The catheter, which may be either a single unit or two-piece in design, has a central lumen consisting of a plastic tube approximately 100 cm long to which is affixed at its distal end a metallic or plastic inner ring. The inner ring is shaped in a conical manner with the base of the cone directed distally with respect to the catheter.

The central lumen of this catheter contains either a stiffening wire or a spring. At the distal end of the stiffening wire or spring is attached either a fixing needle or screw, which consists of a central wire core of approximately 0.010-inch diameter stainless steel and to which are attached a plurality of temperature sensors. The needle or screw may be retractable or fixed. Typically, at least two thermocouples are affixed to the fixation wire at the distal end at predetermined locations from the distal tip of the wire. This assembly is enclosed in a polytetrafluroethylene (PTFE) tubular sheath and then in a stainless steel sheath extending from a Y-connector. The distal end of the centrally aligned fixation wire assembly also serves as one pole of a bipolar sensing probe and is used to monitor the effect of the tissue irradiation both electrophysiologically and thermally.

An outer sheath, typically 6 French in diameter, is used to house the tip assembly and the inner tubular sheath, and is made of a plastic tube to which is attached, at its distal end, an outer brass ring. The outer brass ring may serve as the second pole of the bipolar sensing element. Other sensing elements may be mounted on the exterior of the outer sheath near its distal end. The annular space between the inner and outer tubes, or sheaths, serves as a conduit for flushing/cooling media such as sterile saline solution. This liquid cools both the instrument and tissue and further cools the tissue and removes blood from the field of view of the laser energy during the irradiation process. The liquid exits the catheter through openings or pores in the catheter tip.

Also contained within the annular space of the inner and outer plastic tubes are a plurality of optical fibers for carrying the laser energy to the tissue to be irradiated, such as myocardial tissue. At the distal end, the fibers are configured such that they angle away from the axis of the catheter. This provides a more diffuse pattern of the laser energy than the pattern ordinarily associated with an optical fiber. In this way, a larger surface area is irradiated than is possible with a single fiber. Multiple fibers also provide a catheter having a lower axial stiffness than single fiber systems for a given total energy capacity, thus providing greater catheter flexibility and better maneuverability during use.

Also affixed to the inner wall of the outer sheath near the distal end of the plastic catheter tube may be one or a plurality of steering wires. These steering wires are pushed or pulled, thus altering the geometric shape of the distal end of the catheter, better enabling passage through the vascular system to the treatment site.

At the proximal end of at least one embodiment of the present invention is a multiple-arm Y-connector. The central port of the Y-connector contains the interface for the fixation wire, which consists of two distinct parts. A mechanical plunger extends from the most proximal branch for retracting the fixation wire. Attached to the inner part of the plunger can be two optional thermocouple junction blocks. These junction blocks allow for quick connection of the temperature sensors at the tip of the fixation wire to their measuring instruments.

One branch of the Y-connector is attached to the annular space between the inner and outer plastic tubes. This port is used to pass a coolant and flushing medium along the fibers and out through the tip. This flow cools the components of the delivery device to prevent mechanical degradation or loss of structural integrity from overheating and bathes the myocardial tissue being treated, thereby cooling the tissue and instrument and removing blood from the field of laser energy during irradiation. This flushing helps prevent photocoagulation of blood and reduces tissue surface temperature, reducing the likelihood of carbonization and vaporization.

The other branch of the Y-connector houses the multiple optical fibers. This connection seals against fluid flow and fixes the optical fiber relationship to the laser delivery device.

A metal ring is provided at one of the Y-connector ports which provides an electrical connection to the tip of the laser catheter. The tip can then be used as an electrode for electrophysiological monitoring of cardiac potentials and delivery of radio wave energy to adjacent tissues.

Significant aspects and features of the present invention include the diffusion of concentrated laser light, a flexible catheter, dynamic monitoring of thermal response of the tissue, the use of standard fibers, a larger planar area of treatment, fixation means, and a simple distal tip yielding a smaller, more reliable catheter.

Having thus described the embodiments of the present invention, it is the principal object hereof to provide a multi-fiber laser catheter including temperature sensing means, cooling means, fixation means and flushing means. It is emphasized that the following embodiments in no way limit the perceived and intended scope of the invention.

BRIEF DESCRIPTION OF THE DRAWINGS

Many of the attendant advantages of the present invention will be readily appreciated as they become better understood by reference to the following detailed description when considered in connection with the accompanying drawings, in which like reference numerals designate like elements throughout the figures thereof and wherein.

DETAILED DESCRIPTION OF PREFERRED EMBODIMENTS

Figure 1:
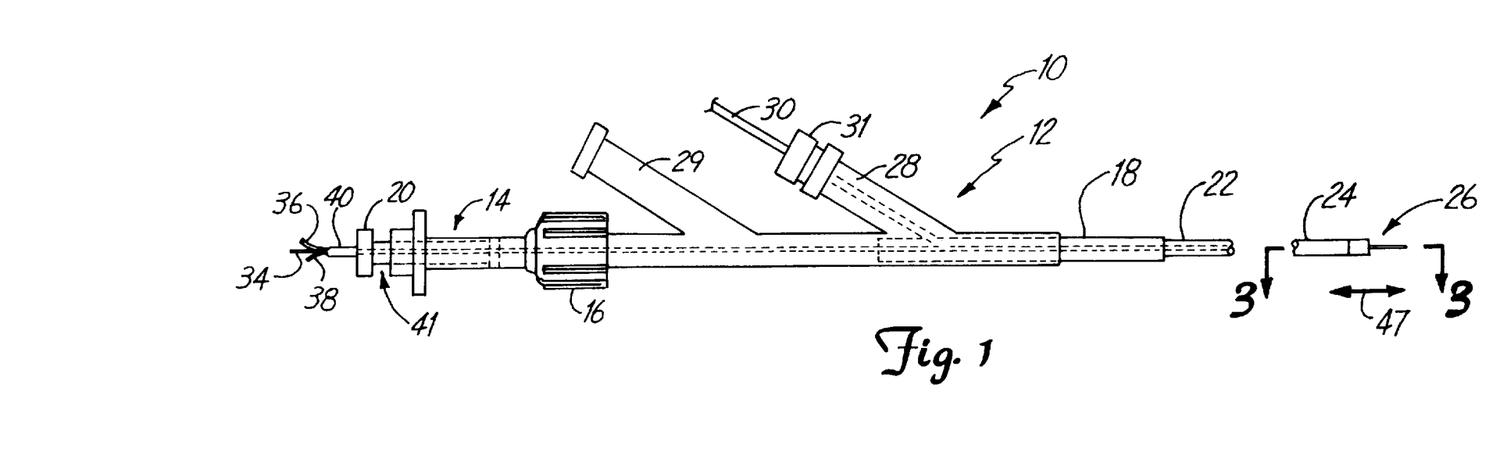
FIG. 1 illustrates a plan view of a multi-fiber laser catheter of the present invention.

FIG. 1 illustrates a plan view of a multi-fiber laser catheter shown generally at 10. This embodiment, as well as the majority of the embodiments described in detail below, are designed to be used as central or inner catheters in a multi-piece catheter system. As mentioned in previous sections, such systems comprise an outer catheter, typically with both steering and electrophysiological mapping capabilities. According to a standard treatment protocol, the outer catheter of the assembly is surgically inserted into and through the patient's vascular system to the heart. Once positioned within the heart, mapping means such as electrodes capable of sensing the electrophysiological properties of endocardial tissue are used to determine the approximate location of tissue to be treated. Once a general electrophysiological map of the heart tissue in the treatment area is obtained, the central, inner treatment catheter according to the design of the present invention is introduced into and through the outer catheter to the heart. Once so positioned the tip of the catheter is maneuvered to more precisely map the specific tissue sites for subsequent irradiation.

Multi-fiber laser catheter 10 includes a dual port Y-connector 12 and a syringe 14 coupled to each other by a coupler nut 16. Stainless steel tube 18 is rigidly affixed to and extends from the distal end of the dual port Y-connector 12. Syringe plunger 20 is integral to syringe plunger tube 41 which slidably resides within syringe 14.

The proximal end of plastic catheter tube 22, about 100 cm in length, secures to the distal end of stainless steel tube 18. The proximal end of annular metallic tip 24 secures to the distal end of plastic catheter tube 22. An axially movable fixation wire assembly 26 extends through and from annular metallic tip 24. Multi-fiber optic cable 30 passes through metallic plug 31 of the dual port Y-connector 12 and through access port 28 into the distally-divided portion of the catheter.

The distal end of stainless steel tube 18 is coupled to the proximal end of plastic catheter tube 22. The distal end of plastic catheter tube 22 is then coupled to the proximal end of annular metallic tip 24. A plurality of wires, including wires 34, 36 and 38, are enclosed within stainless steel tube 40 and extend from the proximal end thereof. Stainless steel tube 40 is enclosed within and axially aligned with syringe plunger tube 41, and syringe 14, terminating within and axially aligned with dual port Y-connector 12. Extending from the distal end of stainless steel tube 40, wires 34, 36 and 38 are further enclosed within the remaining distal end of the body of dual port Y-connector 12, stainless steel tube 18 and plastic catheter tube 22, terminating within annular metallic tip 24 as later described in detail. Wire 34 is a stiffening wire and wires 36 and 38 are wires leading from thermocouples on fixation wire assembly 26 to external monitoring and control equipment.

Flush port 29 of dual port Y-connector 12 is a fluid port, and is connected to the interior body of dual port Y-connector 12. The interior walls of flush port 29 define an axially-disposed lumen that adjoins the lumen within dual port Y-connector 12, which is in open communication with the lumen defined by the inner walls of stainless steel tube 18. This lumen, in turn, communicates with the lumen within attached plastic catheter tube 22, forming a continuous conduit for conducting flushing/cooling fluid through the catheter and to the site of irradiation. A fluid is thereby routed through flush port 29, through stainless steel tube 18, along multi-fiber optic cable 30 through plastic catheter tube 22 and out of annular metallic tip 24 as described later in greater detail.

Figure 2:
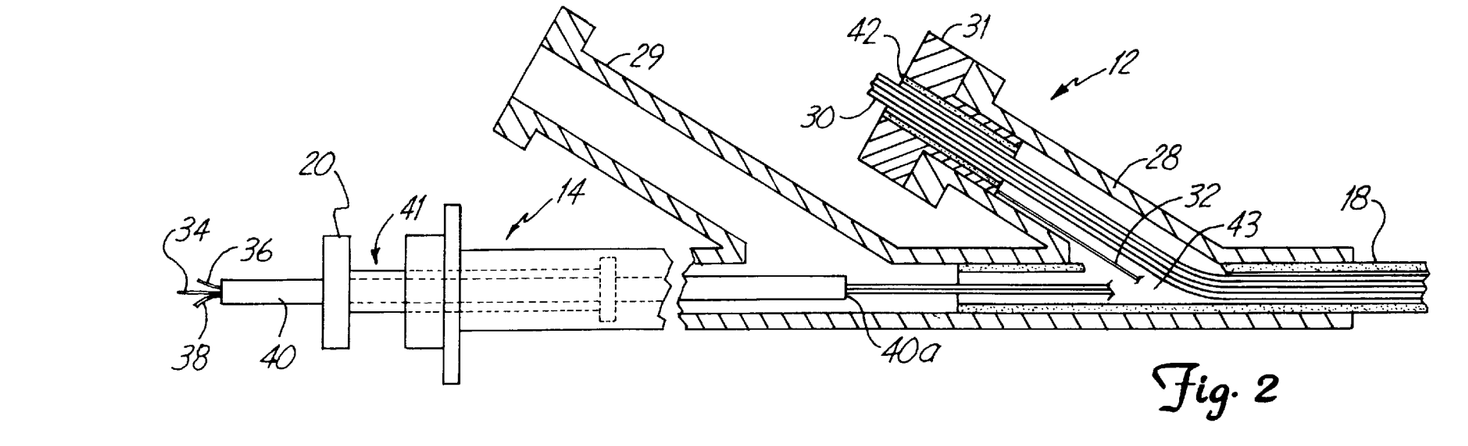
FIG. 2 illustrates a cross-sectional view of the syringe and Y-connector.

FIG. 2 illustrates a partial cross-sectional view of syringe 14 and dual port Y-connector 12. All numerals correspond to those elements previously described. Stainless steel tube 40 aligns coaxially within and rigidly affixes to syringe plunger tube 41. Wires 34, 36 and 38 align in, and are secured within, a lumen of stainless steel tube 40.

Figures 3, 4, 5:
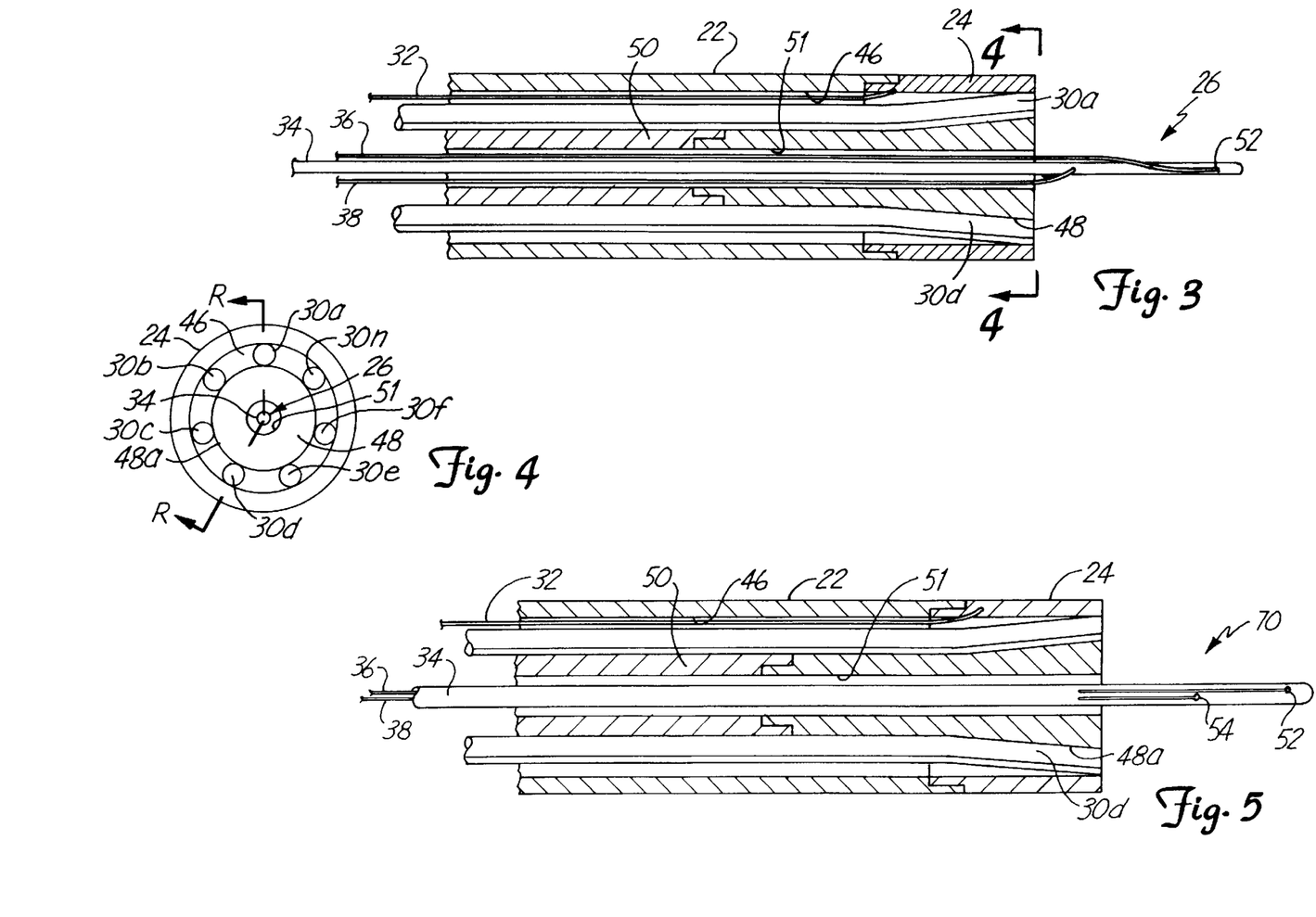
FIG. 3 illustrates a cross-sectional view of the catheter tip area along line 3—3 of FIG. 1.
FIG. 4 illustrates a distal view along line 4—4 of FIG. 3.
FIG. 5 an alternative embodiment with a fixed tip, illustrates a cross-sectional view of the distal end including a fixed thermocouple assembly.

Multi-fiber optic cable 30 aligns within metallic plug 31, tubular plastic member 42, and port 28 of dual port Y-connector 12, and also within lumen 43 of stainless steel tube 18. Multi-fiber optic cable 30 shares lumen 43 with wires 34, 36, and 38, all of which align in lumen 43 within stainless steel tube 18, and in the central lumen 46 of plastic catheter tube 22 as illustrated in FIG. 3. Actuation of syringe plunger 20, and hence attached stainless steel tube 40, causes wires 34–38, which ultimately make up the majority of the structure in the fixation wire assembly 26 (see FIG. 1), to move axially as depicted by double arrow 47.

Wire 32 (FIGS. 2–3), which is an example of a fixation element, aligns in access port 28 of dual port Y-connector 12, connecting electrically to outer metallic ring (or tip) 24. Wire 32 is further enclosed within stainless steel tube 18 and plastic catheter tube 22, connecting electrically to annular metallic tip 24, thereby providing a means of recording electrical potentials inside the heart. Bipolar mapping can be carried out by measuring local activation potentials of the endocardial surfaces. In conjunction with standard electrophysiological monitoring equipment, mounted externally to the catheter, the signals generated can be used to determine electrophysiological properties of the tissue that lies between the electrodes. During denaturation these signals can be monitored for changes.

FIG. 3 illustrates a cross-sectional view of the catheter tip area along line 3—3 of FIG. 1. All numerals correspond to those elements previously described. The proximal end of metallic tip 24, preferably constructed of brass or stainless steel, is step-reduced to a smaller radius so that it will frictionally engage a correspondingly-shaped structure integral to the distal end of plastic catheter tube 22. The interior surface of conically shaped member 48 forms a central passageway, which aligns coaxially within annular metallic tip 24 and is aligned longitudinally with and mated to an inner sheath or tubing 50.

The interior walls of tubing 50 and conically shaped member 48 define a lumen 51. Tubing 50 and member 48 are, in turn, enclosed within plastic catheter tube 22. Conically ramped surface 48a of conically shaped member 48 causes the alignment of individual optic fibers 30a–30n of multi-fiber optic cable 30 to diverge from the alignment of the central axis and to be distributed more closely adjacent to the inner circumference of annular metallic tip 24. Wire 32 is electrically connected to metallic tip 24 and passes through an annular lumen 46, circumscribed by the interior surface of tube 22 and tip 24, to dual port Y-connector 12, as previously described.

Fixation wire assembly 26 co-axially aligns in lumen 51 and includes thermocouples 52 and 54 embedded or otherwise attached thereto. The entire assembly is free to move slidably within lumen 51, as actuated through movement of syringe plunger 20 at the proximal end of the catheter. The thermocouples of the assembly are used to monitor tissue temperature during irradiation at multiple depths within the tissue. Typically, irradiation of tissue is ceased by a termination device when tissue temperatures, as sensed by the thermocouples, reach about 150° C. Such termination of irradiation can be achieved by an operator-triggered termination device based on visual monitoring of the temperature signal provided by external monitoring equipment by the thermocouples. Alternatively, cessation of irradiation may be triggered automatically by appropriate termination device control circuits in a feedback communication loop with the temperature signal generated by the thermocouples. In practice, such automatic control means can be pre-set or programmed to signal cessation of irradiation when monitored temperature of the tissue being irradiated reaches a pre-determined value. A significant advantage in the case of multiple thermocouples on fixation probe 26 is that a temperature depth profile for the treated tissue may be generated. When such data is used in a feedback control circuit, it is possible to program such control means to respond to a temperature signal from an individual thermocouple (and thus to a temperature at a pre-determined depth within the treated tissue) or to a variety of alternative signals such as the difference in temperatures between any two thermocouples, the rate of change of temperature between any individual combination of thermocouples, etc. Thus, a degree of control of the denaturation process can be achieved that has been heretofore impossible within the art.

Inner sheath or tubing 50 encloses wires 34, 36 and 38, and terminates within stainless steel tube 18, as shown in FIG. 1. Wire 34 is connected to and is integral with the shaft of fixation wire assembly 26. Wires 36 and 38 connect electrically to thermocouples 52 and 54, respectively, and are routed within inner tubing 50, dual port Y-connector 12, and end 40a of stainless steel tube 40 as previously described. Fixation wire assembly 26 contains a plurality of thermocouples, including thermocouples 52 and 54. Preferably, at least two thermocouples are used to provide more complete data and are located along the fixation wire such that, upon penetration of the fixation wire into the tissue, the thermocouples are situated within tissue being irradiated to the highest temperature. Fixation wire assembly 26 is also adapted for electrical connection to one pole of the bipolar sensing system. Thus, the fixation wire is capable of providing a plurality of functions within the catheter of the present invention: mechanical fixation to the tissue site; one pole of a bipolar electrophysiological mapping system; and a temperature probe for generating a temperature depth profile of the treated tissue. Metallic tip 24 provides an electrical connection for the second pole of the electrophysiological mapping system.

The annular space between outer plastic catheter tube 22 and inner plastic tube (or sheath) 50 serves as a conduit for flushing/cooling media such as sterile saline solution. This liquid cools the tissue and metallic tip 24, as well as the individual optical fibers, and removes blood from the field of laser energy during irradiation.

Because of the need to pass through a long and narrow anatomical passageway so that metallic tip 24 is placed correctly with respect to the tissue site to be irradiated, fixation wire assembly 26 is typically retracted into metallic tip 24 during advancement of the catheter. Preferably, the wire is coated with a non-stick coating such as TEFLON™ to facilitate sliding within inner lumen 51. With fixation wire assembly 26 retracted, metallic tip 24 presents a very low profile device whose leading edge is smooth and free of protrusions which would cause the catheter to snag or hang-up during its passages through portions of anatomy en route to the treatment site. Upon reaching the desired treatment site, fixation wire assembly 26 is deployed to penetrate the myocardial surface, thereby holding the tip in place so that irradiation of only targeted tissue may proceed within the continuously moving surface of the beating heart. Fixation wire assembly 26 may also serve as one component of a bipolar mapping assembly as mentioned above.

FIG. 4 illustrates a view along line 4—4 of FIG. 3. All numerals correspond to those elements previously described. Illustrated in particular is the distribution of the individual fiber optic cables 30a–30n about the inner circumference of annular metallic tip 24. Sterile cooling/flushing fluid passes through lumen 46 as defined by the inner circumference of annular metallic tip 24 and the outer, conically shaped surface of member 48, as illustrated in FIG. 3.

Cooling, sterile flushing fluid flow continues along and between ramped surface 48a and the interior circumference of annular metallic tip 24, as well as along individual fiber optic members 30a–30n, exiting between the areas aligned with the ends of individual fiber optic members 30a–30n, and the inner circumference of metallic tip 24 and the largest diameter of conical member 48.

FIG. 5 illustrates an alternative, fixed-needle embodiment of the distal end of the catheter system including a fixed, fixation wire assembly 70. All numerals correspond to those elements previously described. The fixation wire assembly is fixed in the position illustrated and is used in an environment where retraction of the fixation wire is not required. Such design results in a considerable simplification of both manufacture and function, obviating the need for the proximally-oriented syringe assembly of the previously described embodiment.

Figure 6:
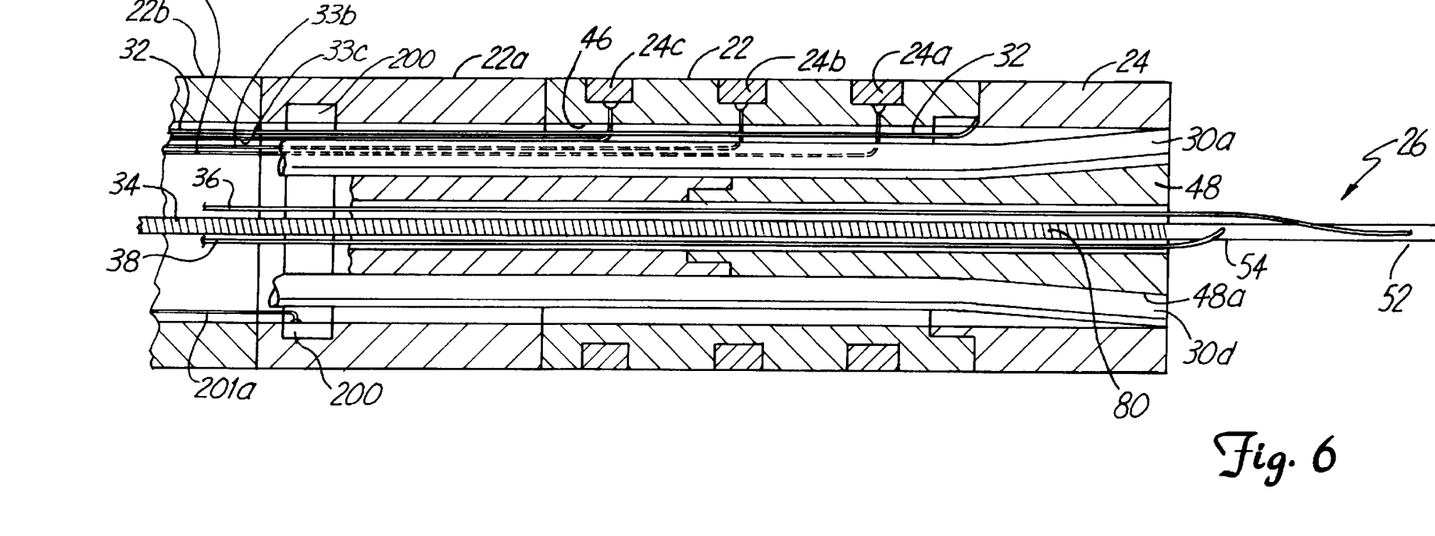
FIGS. 6–6A illustrate an alternate embodiment, a steerable multi-fiber laser catheter depicted in a cross-sectional view of the distal and proximal ends.

FIG. 6 depicts a cross-sectional view of an alternate embodiment of the present invention, a steerable multi-fiber laser catheter for use in cardiac tissue irradiation. All numerals correspond to those elements previously described. While prior art embodiments have been designed as part of two-piece ablation systems in which an ablation catheter is separate from a steerable mapping catheter, the present embodiment of the invention combines the function of the two-piece system into a steerable, single-piece mapping and irradiation catheter. The central element is a movable fixation wire assembly 26 which contains a plurality of temperature sensors as described for the embodiment illustrated in FIG. 3. The distal-most portion of the wire is a solid metal tube for structural stability, to both penetrate myocardial tissue, which may be scarred, and minimize motion of the catheter during ablation in a continuously beating heart. Proximally adjoining and affixed to the solid portion of the central movable fixation wire is a spring-type tube 80 made of a thin, coiled wire. This design provides the requisite axial stiffness and compressibility without the penalty of unbending stiffness, making the catheter easier to steer while inside the heart. The multi-fiber array is the same as previously described for earlier embodiments in FIGS. 1, 2 and 3.

The exterior tip of this embodiment contains the mapping and steering functions generally embodied in the outer catheters used with the alternative embodiments of the invention. Three ring electrodes 24a, 24b and 24c, are embedded into the exterior of the plastic catheter tube 22 to provide an enhanced means for mapping the endocardial surface and thereby determine optimal sites for irradiation. Additionally, more electrodes could be added to further enhance the mapping capabilities of the catheter. Each electrode is connected to the proximal end via a single wire per electrode, as shown at 33a–33c, which wires follow the same path through lumen 46 as the individual optical fibers 30a–30n and connecting at the proximal end to sensing equipment (not shown) external to the catheter. In addition, annular metallic tip 24 also functions as a sensing electrode in this embodiment.

Figure 6A:
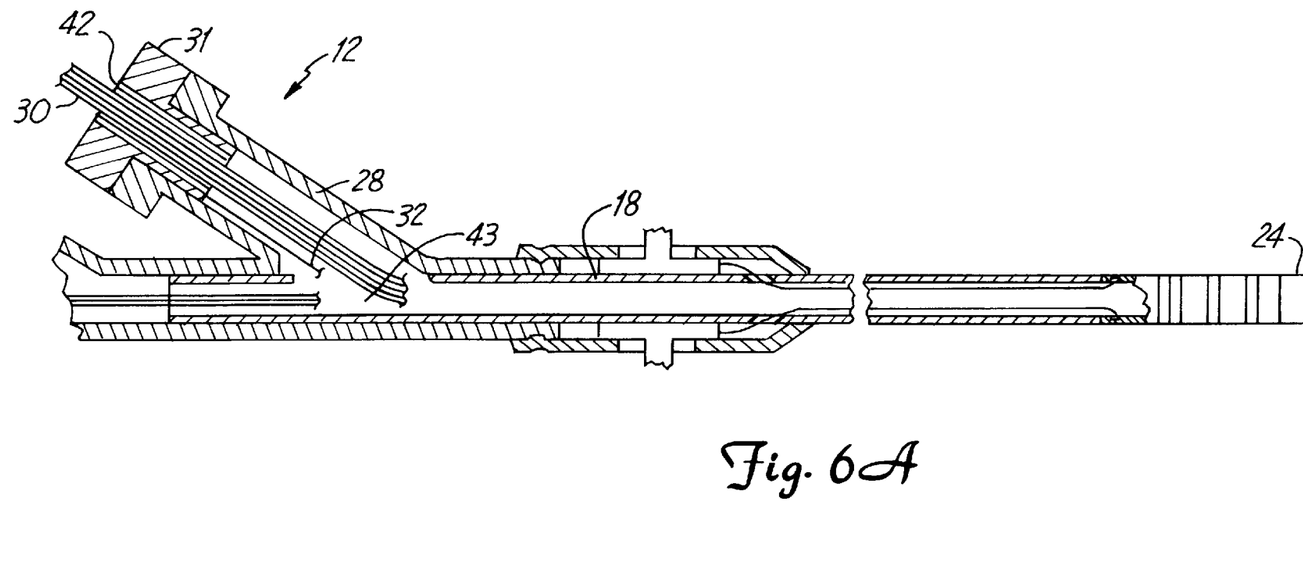

Anchoring ring 200 is embedded in the inner walls of the catheter shaft toward the distal portion of the catheter. The hardness of the plastics in this tip region of articulation can be tailored to give the desired geometric size and shape to the bend. Element 200 is an anchor point for push/pull wires 201a and 201b (see FIG. 6A). Wires 201a and 201b follow the same path through lumen 46 to the dual Y-port as optical fibers 30a–30n, unless they are connected to a mechanism mounted on the exterior of the dual port Y connector, as depicted in FIG. 6A. This mechanism comprises a push-pull switch that can be operated normally to exert push/pull forces on steering wires 201 and 201b. In practice, either one or both wires can be used. In a two wire system, one wire is pulled while the other wire is pushed. The difference in force between the wires translates to a bending motion in the direction of the highest tension. Return to the original shape is accomplished by curving the catheter in a pushing mechanism for straightening the catheter tip. By altering the force on the wires, the position of the anchor rings, and the hardness of the plastics, the ultimate shape of the distal tip of the catheter can be changed. The overall functioning of the system to perform irradiation of cardiac tissue is essentially the same as that previously described. However, this catheter is capable of performing both the locating and ablating functions of this invention.

FIGS. 7, 8, 9 and 10 depict still another embodiment of this invention, a multi-fiber laser catheter with a non-movable fixation probe. All numerals correspond to those elements previously described. In this embodiment, the fixation probe and temperature sensing elements are fixed within the multi-fiber catheter; therefore, the needle is no longer slidably movable within the laser catheter. The advantages of this design are ease of manufacturing, ease of use and possibly more accurate tissue temperature measurement.

Figure 7:
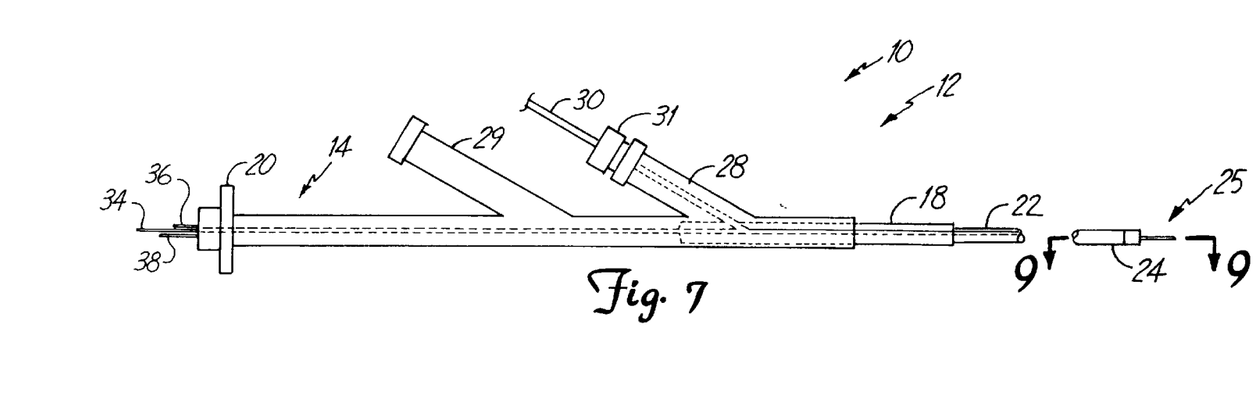
FIG. 7 provides another alternate embodiment, a one-piece, fixed needle multi-fiber laser catheter, illustrated in a plan view of a multi-fiber laser catheter.

In FIG. 7, stiffening wire 34 runs continuously from the distal to the proximal ends of the apparatus. All numerals depicted in FIG. 7 correspond to those elements previously described.

Figure 8:
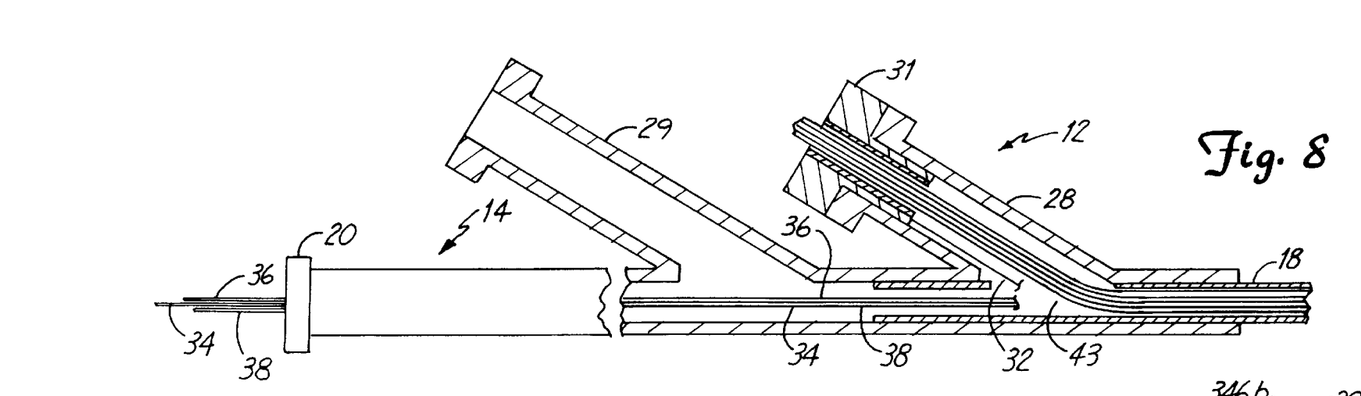
FIG. 8 illustrates a cross-sectional view of the syringe and dual port Y-connector of the embodiment depicted in FIG. 7.

FIG. 8 illustrates a cross-sectional view of the syringe and dual port Y-connector of the embodiment depicted in FIG. 7. All numerals correspond to those elements previously described.

Figures 9, 10:
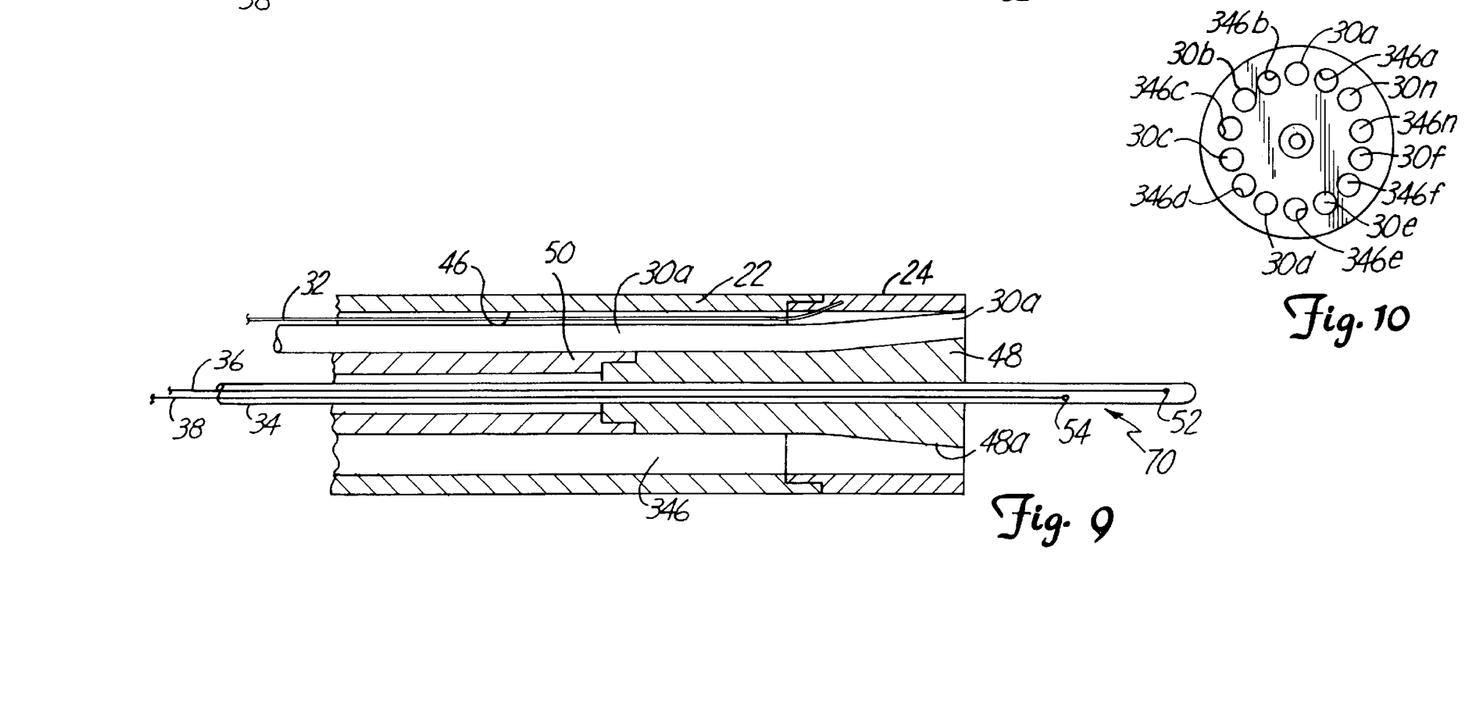
FIG. 9 illustrates a cross-sectional view of the catheter tip area of the embodiment depicted in FIG. 7.
FIG. 10 illustrates a distal view of the catheter tip of the embodiment depicted in FIG. 7.

FIG. 9 illustrates a cross-sectional view of the catheter tip area of the embodiment depicted in FIG. 7 along lines 9—9. All numerals correspond to those elements previously described. In FIG. 9 is shown a flushing port lumen 346 formed within the catheter between the interior surface of catheter tube 22 and the exterior surface of inner tubing 50. Also depicted in FIG. 9 is the distal end of the fixed needle. At the distal end of the fixed needle are thermocouples 52 and 54. Connecting thermocouples 52 and 54 are wires 36 and 38. The wires 36 and 38 connect to thermocouples 52 and 54 and enter into the lumen within tube 334 and proceed therethrough as previously described.

FIG. 10 illustrates a distal view of the catheter tip of the embodiment depicted in FIG. 7. All numerals correspond to those elements previously described. Depicted in FIG. 10 are the flushing ports 346*a* through 346*n*. Because the flow of flushing fluid proceeds over the distal electrodes from alternating ports close to the optical fibers, washing blood and other tissue materials from the field of view is better facilitated. Since the fixation wire assembly cannot be retracted in this embodiment, this type of catheter would only be recommended where smooth edges and possible protrusions are of no consequence.

FIGS. 11, 12, 13 and 14 describe an alternative embodiment of the invention. In this embodiment, the tip is made of a porous metal to allow for more efficient cooling of the instrument as well as prevention of deposits of the tissue being treated onto the catheter tip. The tip of the fixation wire is constructed in a helical configuration and is rotated within the catheter to screw the fixation needle into the tissue, thereby more firmly affixing the catheter to the wall of the beating heart.

Figure 11:
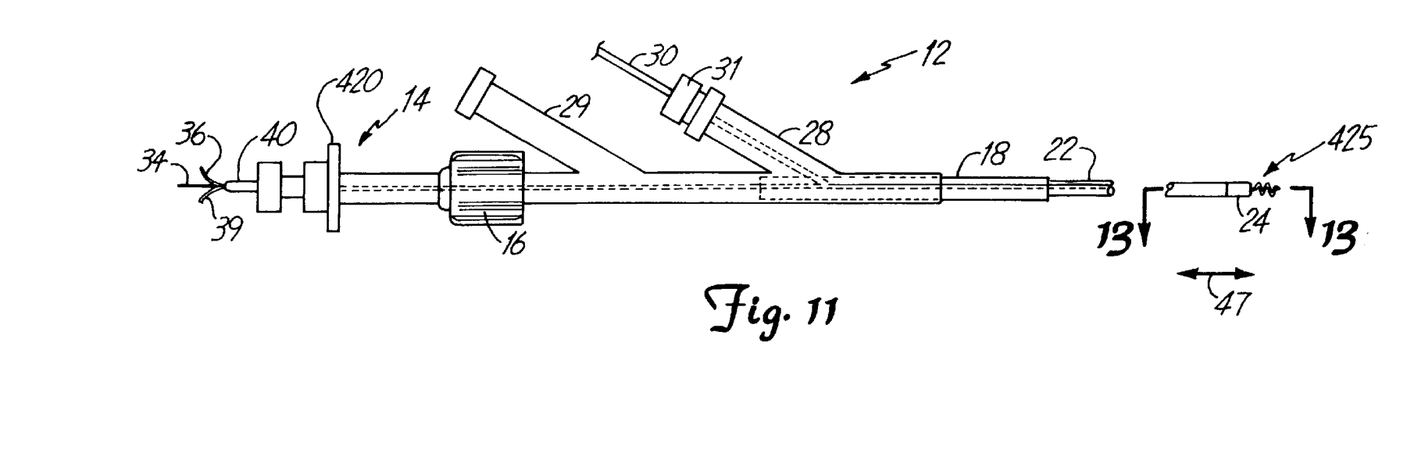
FIG. 11, illustrative of another embodiment, provides a plan view of a multi-fiber laser catheter with a rotational, helical fixing assembly and a porus tip.

FIG. 11 illustrates a plan view of a multi-fiber laser catheter with a rotational, helical fixing assembly and a porus tip. All numerals correspond to those elements previously described. In FIG. 11, syringe plunger 420 is connected to stainless steel tube 40. Rotation of the knob of syringe plunger 420 thereby rotates stainless steel tube 40 within syringe 14. Also depicted is the screw-in electrode map thermocouple fixation assembly which will be described in greater detail below.

Figure 12:
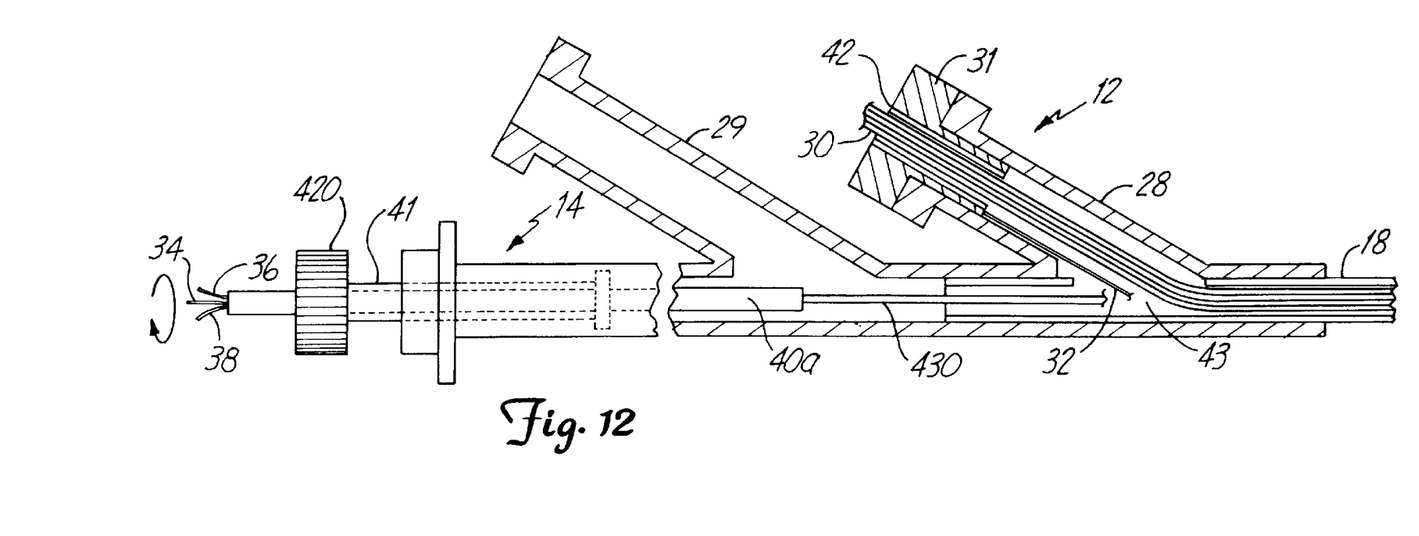
FIG. 12 illustrates a cutaway view of the syringe and dual port Y-connector of the embodiment depicted in FIG. 11.

FIG. 12 illustrates a partial cutaway view of the syringe and dual port Y-connector of the embodiment depicted in FIG. 11. All numerals correspond to those elements previously described. In FIG. 12 is depicted the flexible braided thin wall shaft 430 which is secured to stainless steel tube 40 at its distal end 40*a*. Braided thin-wall shaft 430 provides grater flexibility for lateral bending than wire 34 used in previous embodiments.

Figure 13:
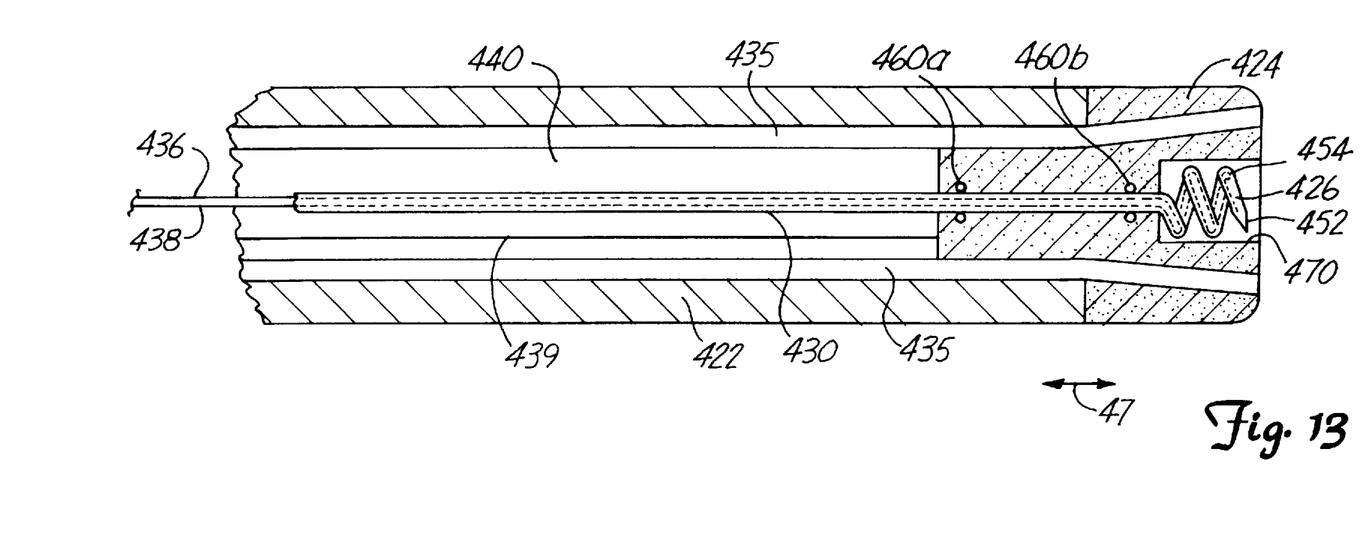
FIG. 13 illustrates a cross-sectional view of the catheter tip area of the embodiment depicted in FIG. 11.

FIG. 13 illustrates a cross-sectional view along line 13—13 of the catheter tip area of the embodiment depicted in FIG. 11. All numerals correspond to those elements previously described. In FIG. 13 is depicted the flush lumen 440 which conducts the flushing medium from the proximal to the distal end of the apparatus. The braided shaft 430 extends to and is connected to the proximal end of the screw-in temperature-sensing fixation assembly 426. The screw-in temperature-sensing fixation assembly 426 is shown as a helical configuration. Mounted on the screw-in temperature-sensing fixation assembly 426 are a plurality of thermocouple devices, two in number as shown here, 452 and 454. The screw-in temperature-sensing fixation assembly 426 can be retracted within recessed port 470. Collars 460*a*, 460*b* prevent backflow of bodily fluids into the catheter tip. Optic fibers 435*a* through 435*n* are enclosed within lumens as previously described. The outer shaft 422 is preferably constructed of the same materials as the plastic catheter tube 22 of FIG. 3. The electrode wire 439 is electrically connected to the proximal end of porus metal tip 426. Thermocouple wires 436 and 438 are connected to thermocouples 452 and 454, respectively, enter the interior of the screw-in temperature-sensing fixation assembly 426 proceed proximally through and inside the braided shaft 430 as discussed with respect to wire 36 and wire 38 previously.

Figure 14:
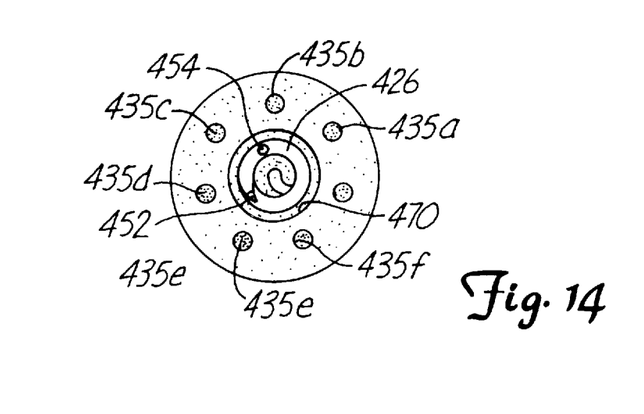
FIG. 14 illustrates a distal view along line 14—14 of FIG. 13 of the catheter tip of the embodiment depicted in FIG. 11.

FIG. 14 depicts a cross-sectional view of the distal end of the embodiment illustrated in FIG. 11. All numerals correspond to those elements previously described. Optical fibers 435*a*–435*n* are evenly distributed on the distal end of the porous metal tip 424, preferably about midway between the outer perimeter of porous metal tip 424, and the exterior edge of recessed port 470. In this embodiment the flushing flow totally surrounds the optical fibers, thereby more thoroughly bathing the treated tissue and apparatus. The screw-in electrode fixation assembly (temperature sensing and fixation arrangement) allows for secure, intimate contact of the catheter tip with the heart tissue, with a good coupling of laser and radio frequency energy irradiation capabilities. The flushing of the distal electrode (or tip) allows the use of radio frequency energy. The use of both radio frequency energy and laser energy allows for ablation of both the surface of the endocardium and deep within the myocardial tissue. Contact fiber lasering tends to cause a pear shaped lesion extending from the fiber contact position corresponding to the top of the pear to the full depth of the myocardium. In contrast, the use of radio frequency energy allows for a more cylindrically shaped, rather than pear-shaped lesion.

Changes and modifications in the specifically described embodiments can be carried out without departing from the scope of the invention which is intended to be limited only by the scope of the claims thereof.

What is claimed is:

1. A laser catheter, for use in providing therapeutic laser energy to human heart tissue at a pre-selected tissue site, the catheter comprising:

a) a catheter body having a proximal end and a distal end and an inner wall defining a lumen extending generally along a longitudinal axis of said catheter;

b) a multi-fiber optic cable having a proximal end and a distal end located within said catheter body and having a plurality of individual optical fibers to provide laser energy to the tissue site by a laser source;

c) a fixation element, having a proximal end and a distal end and operably carried through said lumen extending past said distal end of said catheter body, constructed to selectively penetrate the tissue to a predetermined depth at said pre-selected tissue site and to fix said distal end of said catheter body to said tissue; and d) a plurality of temperature sensors, fixedly attached at spaced intervals along the length of said fixation element within the tissue to sense the temperature of said tissue at a plurality of tissue depths corresponding to said spaced intervals while said laser catheter is providing laser energy to said pre-selected tissue site, wherein said plurality of temperature sensors provide temperature readings correlated to the tissue depth at which each temperature sensor is located to create a temperature depth profile of the tissue.

2. The catheter of claim 1, further comprising a laser energy termination device, operably coupled to the plurality of temperature sensors and to the laser source and adapted to terminate provision of laser energy to the tissue site based on temperature readings from at least two of the temperature sensors.

3. The catheter of claim 2, wherein the termination device comprises feedback control circuitry.

4. The catheter of claim 2, wherein the termination device is triggered by an operator.

5. The catheter of claim 1, further comprising an electrophysiological mapping system operably coupled with the catheter body, the fixation element being one pole of the electrophysiological mapping system.

6. The catheter of claim 5, further comprising a metallic tip at the distal end of the catheter body, the metallic tip being a second pole of the electrophysiological mapping system.

7. The catheter of claim 1, wherein the catheter is a one-piece catheter.

8. The catheter of claim 1, wherein the catheter is a multi-piece catheter.

9. A laser catheter for use in a multi-piece catheter system, the laser catheter providing controlled laser energy effective to therapeutically denature human heart tissue at a pre-selected cardiac tissue site, the catheter comprising:

a) a catheter body having a proximal end and a distal end, and an inner wall defining a first lumen extending generally along a longitudinal axis of the catheter;

b) a multi-fiber optic cable having a proximal end and a distal end located within the catheter body and having a plurality of individual optical fibers to provide laser energy to the tissue site by a laser source;

c) substantially helically-shaped fixation means, aligned co-axially with and contained within the catheter body, for penetrating a controlled depth into cardiac tissue at the pre-selected tissue site and fixing the catheter to the site, the fixation means having a proximal end and a distal end and a length sufficient to extend beyond the distal end of the catheter body; and d) a plurality of temperature sensing means, fixedly attached to the fixation means at spaced intervals from the distal end of the fixation means and operably connected to the laser source, for sensing a plurality of temperatures, at depths within the cardiac tissue corresponding to the spaced intervals, while the laser catheter is providing radiant energy to the tissue site, wherein the plurality of temperature sensing means provide temperature signals which correlate to the tissue temperature at the location of each temperature sensing means, and wherein the temperature signals are used to control irradiation of the tissue site.

10. The catheter of claim 9, wherein the temperature signals control the irradiation of the tissue site by terminating irradiation of the site when the signals indicate that the tissue at the site has reached a predetermined temperature.

11. The catheter of claim 10, wherein the predetermined temperature is 423° K.

12. The catheter of claim 9, further comprising a metal tip operably coupled to the distal end of the catheter body, the plurality of optical fibers passing through the metal tip, the metal tip holding the distal ends of the optical fibers in an orientation divergent from the longitudinal axis of the catheter.

13. The catheter of claim 12, further comprising access means, located toward the proximal end of the catheter body, for operable communication with the first lumen of the catheter body.

14. The catheter of claim 13, wherein the access means comprises a plurality of separate access ports, each port being in operable communication with the first lumen.

15. The catheter of claim 13, further comprising an electrically conducting wire fixably attached at a distal end to the metal tip of the catheter, the wire extending axially through the inner lumen of the catheter body to and through the access means.

16. The catheter of claim 13, further comprising means for directing a fluid cooling/flushing medium through the access means to the inner lumen of the catheter body.

17. The catheter of claim 9, wherein the fixation means is fixed within the catheter body and wherein the distal end of the fixation means extends a fixed amount beyond the distal end of the catheter.

18. The catheter of claim 9, wherein the fixation means is slidably located within the catheter body.

19. The catheter of claim 18, further comprising mechanical control means affixed to the proximal end of the catheter and operably coupled to the fixation means for slidably extending the distal end of the fixation means beyond the distal end of the catheter body and back within the catheter body.

20. The catheter of claim 19, further comprising a tube aligned centrally within the control means and extending co-axially through the catheter body to the distal end of the catheter body, the tube comprising inner walls that define a second lumen, the fixation means passing through the second lumen.

21. The catheter of claim 20, further comprising a plurality of electrically conducting wires, each wire having a distal end and a proximal end, wherein the distal end of each wire is connected to a respective one of the plurality of temperature sensing means attached to the fixation means, wherein the plurality of wires is aligned axially with the second lumen, each of the plurality of wires extending through the second lumen and out from the proximal end of the catheter body.

22. A one-piece laser catheter system, providing controlled laser energy effective to therapeutically denature human heart tissue within a patient's heart without ablating that tissue, the catheter system comprising:

a) a catheter body having a proximal end and a distal end, and an inner wall defining a first lumen extending generally along a longitudinal axis of the catheter;

b) a multi-fiber optic cable having a proximal end and a distal end located within the catheter body and having a plurality of individual optical fibers to provide laser energy to a pre-selected treatment site by a laser source;

c) a metal tip operably coupled to the distal end of the catheter body, the plurality of optical fibers passing through the metal tip, distal ends of the optical fibers being held in an orientation divergent from the longitudinal axis of the catheter body by the metal tip;

d) fixation means, aligned coaxially with and contained within the catheter body, for penetrating a controlled depth into cardiac tissue at the pre-selected treatment site and fixing the catheter to the site, the fixation means having a proximal end and a distal end and a length sufficient to extend beyond the distal end of the catheter body;

e) a plurality of temperature sensing means, fixedly attached to the fixation means at spaced intervals along the fixation means within the cardiac tissue, for sensing a plurality of temperatures at depths within the cardiac tissue corresponding to the spaced intervals while laser energy is being provided to the tissue site, wherein the plurality of temperature sensing means provide temperature signals which correlate to the tissue temperature at the location of each temperature sensing means, and wherein the temperature signals are used to control irradiation of the tissue site and to create a temperature depth profile of the cardiac tissue;

f) electrophysiological sensing means, located on the external surface of the catheter body, for sensing the electrophysiological characteristics of cardiac tissue proximate to the sensing means; and g) steering means for guiding the catheter system through anatomical structures within the patient's body to the interior of the heart, the steering means being operatively coupled to an externally accessible steering control device for controlling steering of the catheter through the anatomical structures.

23. The system of claim 22, wherein the temperature signals control the irradiation of the tissue site by terminating irradiation of the site when the signals indicate that the tissue at the site has reached a pre-determined temperature.

24. The system of claim 22, wherein the fixation means is slidably located within the catheter body.

25. The system of claim 24, further comprising mechanical control means affixed to the proximal end of the catheter and operably coupled to the fixation means for slidably extending the distal end of the fixation means beyond the distal end of the catheter body and back within the catheter body.

26. The system of claim 25, further comprising a tube aligned centrally within the control means and extending co-axially through the catheter body to the distal end of the catheter body, the tube comprising inner walls that define a second lumen, the fixation means passing through the second lumen.

27. The system of claim 26, further comprising a plurality of electrically conducting wires, each wire having a distal end and a proximal end, wherein the distal end of each wire is connected to a respective one of the plurality of temperature sensing means attached to the fixation means, wherein the plurality of wires is aligned axially with the second lumen, each of the plurality of wires extending through the second lumen and out from the proximal end of the catheter body.

28. The system of claim 22, further comprising access means, located toward the proximal end of the catheter for operable communication with the first lumen of the catheter.

29. The system of claim 28, further comprising means for directing a fluid cooling/flushing medium through the access means to the inner lumen of the catheter body.

30. The system of claim 22, wherein the metal tip is a porous metal tip.

31. The laser catheter of claim 22, wherein the distal end of the fixation means is helically shaped.

32. The laser catheter of claim 31, further comprising mechanical control means affixed to the proximal end of the catheter and operably coupled to the fixation means for slidably extending the helically shaped distal end of the fixation means beyond the distal end of the catheter body and back within the catheter body.

33. The laser catheter of claim 32, wherein the control means rotatably moves the distal end of the helically shaped fixation means to securely fix the fixation means to the cardiac tissue.

34. A method for the controlled laser irridation of cardiac tissue at a pre-selected tissue site to therapeutically denature cardiac tissue at the site, the method comprising:
(a) introducing a distal end of a laser catheter proximate to the pre-selected cardiac tissue site;
(b) denaturing cardiac tissue at the pre-selected tissue site by irradiating the cardiac tissue with laser energy provided via the catheter by a laser source;
(c) fixing the distal end of the catheter to the pre-selected tissue site by penetrating cardiac tissue at the pre-selected tissue site with a fixation element extending from the distal end of the catheter;
(d) flushing the pre-selected tissue site with a fluid flushing medium introduced to the pre-selected tissue site through the catheter; and
(e) monitoring, during step (d), the temperature of the cardiac tissue at the pre-selected tissue site with at least one temperature sensor at the fixation element.

35. The method of claim 34, wherein step (e) includes creating a temperature depth profile of the cardiac tissue at the pre-selected tissue site by a plurality of spaced temperature sensors on the fixation element.

36. The method of claim 34, further comprising electrophysiologically mapping the pre-selected tissue site with the laser catheter to determine a precise location for irradiation of tissue by the laser catheter.

37. The method of claim 36, further comprising steering the laser catheter with an externally accessible steering control device through anatomical structures to the pre-selected tissue site.

38. The method of claim 34, wherein step (b) includes irradiating the cardiac tissue with laser energy provided via a multi-fiber optic cable having a plurality of optical fibers, the optical fibers diverging from a longitudinal axis of the catheter.

39. The method of claim 38, wherein step (d) includes directing the fluid flushing medium along the plurality of optical fibers diverging from the longitudinal axis of the catheter, the flushing flow surrounding the optical fibers to thoroughly bathe the pre-selected tissue site.

40. A method of providing both laser energy and radio frequency energy to denature cardiac tissue at a pre-selected tissue site by a catheter, the method comprising:
(a) introducing a distal end of a catheter proximate to the pre-selected cardiac tissue site;
(b) irradiating the cardiac tissue with laser energy provided via the catheter by a laser source;
(c) irradiating the cardiac tissue with radio frequency energy provided via the catheter by a radio frequency energy source;
(d) flushing the pre-selected tissue site with a fluid flushing medium introduced to the pre-selected tissue site through a porous tip of the catheter;
(e) fixing the distal end of the catheter to the pre-selected tissue site by penetrating cardiac tissue at the pre-selected tissue site with a fixation element extending from the distal end of the catheter; and
(f) monitoring the temperature of the cardiac tissue at the pre-selected tissue site with at least one temperature sensor at the fixation element.

41. The method of claim 40, wherein step (f) includes creating a temperature depth profile of the cardiac tissue at the pre-selected tissue site by a plurality of spaced temperature sensors on the fixation element.

42. A one-piece laser catheter system, providing controlled laser energy effective to therapeutically denature human heart tissue within a patient's heart without ablating that tissue, the catheter system comprising:
a) a catheter body having a proximal end and a distal end, and an inner wall defining a first lumen extending generally along a longitudinal axis of the catheter;
b) a multi-fiber optic cable having a proximal end and a distal end located within the catheter body and having a plurality of individual optical fibers to provide laser energy to a pre-selected treatment site by a laser source;
c) a porous metal tip operably coupled to the distal end of the catheter body, the plurality of optical fibers passing through the metal tip, the distal ends of the optical fibers being held in an orientation divergent from the longitudinal axis of the catheter body by the metal tip;
d) fixation means, aligned coaxially with and contained within the catheter body, for penetrating a controlled depth into cardiac tissue at the pre-selected treatment site and fixing the catheter to the site, the fixation means having a proximal end and a distal end and a length sufficient to extend beyond the distal end of the catheter body;

e) a plurality of temperature sensing means, fixedly attached to the fixation means at spaced intervals from the distal end of the fixation means, for sensing a plurality of temperatures at depths within the cardiac tissue corresponding to the spaced intervals while the laser is providing radiant energy to the tissue site, wherein the plurality of temperature sensing means provide temperature signals which correlate to the tissue temperature at the location of each temperature sensing means, and wherein the temperature signals are used to control irradiation of the tissue site;

f) electrophysiological sensing means, located on the external surface of the catheter body, for sensing the electrophysiological characteristics of cardiac tissue proximate to the sensing means; and g) steering means for guiding the catheter system through anatomical structures within the patient's body to the interior of the heart, the steering means being operatively coupled to an externally accessible steering control device for controlling steering of the catheter through the anatomical structures.

43. A one-piece laser catheter system, providing controlled laser energy effective to therapeutically denature human heart tissue within a patient's heart without ablating that tissue, the catheter system comprising:

a) a catheter body having a proximal end and a distal end, and an inner wall defining a first lumen extending generally along a longitudinal axis of the catheter;

b) a multi-fiber optic cable having a proximal end and a distal end located within the catheter body and having a plurality of individual optical fibers to provide laser energy to a pre-selected treatment site by a laser source;

c) a metal tip operably coupled to the distal end of the catheter body, the plurality of optical fibers passing through the metal tip, the distal ends of the optical fibers being held in an orientation divergent from the longitudinal axis of the catheter body by the metal tip;

d) fixation means, aligned coaxially with and contained within the catheter body, for penetrating a controlled depth into cardiac tissue at the pre-selected treatment site and fixing the catheter to the site, the fixation means having a proximal end and a helically-shaped distal end and a length sufficient to extend beyond the distal end of the catheter body;

e) a plurality of temperature sensing means, fixedly attached to the fixation means at spaced intervals from the distal end of the fixation means, for sensing a plurality of temperatures at depths within the cardiac tissue corresponding to the spaced intervals while the laser is providing radiant energy to the tissue site, wherein the plurality of temperature sensing means provide temperature signals which correlate to the tissue temperature at the location of each temperature sensing means, and wherein the temperature signals are used to control irradiation of the tissue site;

f) electrophysiological sensing means, located on the external surface of the catheter body, for sensing the electrophysiological characteristics of cardiac tissue proximate to the sensing means; and g) steering means for guiding the catheter system through anatomical structures within the patient's body to the interior of the heart, the steering means being operatively coupled to an externally accessible steering control device for controlling steering of the catheter through the anatomical structures.

* * * * *